(12) United States Patent
Sekizawa et al.

(10) Patent No.: US 7,395,726 B2
(45) Date of Patent: Jul. 8, 2008

(54) DISSOLUTION TESTER

(75) Inventors: Kazutoshi Sekizawa, Hachioji (JP); Masao Yamazaki, Hachioji (JP)

(73) Assignee: Jasco Corporation, Hachioji-shi, Tokyo (JP)

( * ) Notice: Subject to any disclaimer, the term of this patent is extended or adjusted under 35 U.S.C. 154(b) by 0 days.

(21) Appl. No.: 11/383,577

(22) Filed: May 16, 2006

(65) Prior Publication Data

US 2006/0260423 A1 Nov. 23, 2006

(30) Foreign Application Priority Data

May 17, 2005 (JP) ............................. 2005-144171

(51) Int. Cl.
*G01N 33/15* (2006.01)
*B01F 1/00* (2006.01)
*B01F 9/12* (2006.01)

(52) U.S. Cl. ..................... 73/866; 73/865.6; 366/241; 366/244; 422/224

(58) Field of Classification Search ............... 73/432.1, 73/864.91, 866, 865.6; 366/140, 241–261; 422/224

See application file for complete search history.

(56) References Cited

U.S. PATENT DOCUMENTS 5,076,107 A * 12/1991 Timmermans et al. ........ 73/866
5,403,090 A * 4/1995 Hofer et al. .................. 366/142
6,962,674 B2 * 11/2005 Dean et al. .................. 422/68.1
2002/0051734 A1 * 5/2002 Dean et al. .................... 422/63

FOREIGN PATENT DOCUMENTS

JP 2000-283977 10/2000

* cited by examiner

*Primary Examiner*—Hezron E. Williams
*Assistant Examiner*—David A. Rogers
(74) *Attorney, Agent, or Firm*—Rankin, Hill & Clark LLP

(57) ABSTRACT

A dissolution tester comprising: a water-tank lid which is provided with a retaining hole having an inner diameter that is slightly larger than the outer diameter of the of the vessel and that is slightly smaller than the outer diameter of the flange of the vessel, and which holds the vessel at the retaining hole; a vessel lid which has a tapered portion having a bottom diameter that is smaller than a top diameter thereof; and a lid-moving shaft which is suspended from a lower part of the head to move up and down together with the vessel lid, when the vessel lid is lowered using the lid-moving shaft to cause the tapered portion of the vessel lid to come into contact with the opening of the vessel, the vessel is made to move such that the center axes of the lid-moving shaft and the vessel are aligned.

4 Claims, 5 Drawing Sheets

DISSOLUTION TESTER

RELATED APPLICATIONS

This application claims priority to the Japanese Patent Application 2005-144171 dated on May 17, 2005 and is hereby incorporated with reference for all purposes.

BACKGROUND OF THE INVENTION

1. Field of the Invention

The present invention relates to dissolution testers, and more particularly, to an improved stabilizing mechanism therefor.

2. Prior Art

Conventionally, in order to ensure consistent quality of drug samples, dissolution tests are conducted to test the dissolution of compounds of interest from those samples.

Various different kinds of dissolution testers have been developed for conducting such tests. For example, one such dissolution tester in the related art is the device described in Japanese Unexamined Patent Application Publication No. 2000-283977.

Dissolution testers generally include a vessel, a paddle (or a rotating basket), a rotary shaft, an electric motor, and a constant-temperature-water tank.

In a dissolution test, a typical sequence of operations carried out with the dissolution tester is as follows. A fixed amount of test liquid is placed in the vessel and the temperature of the test liquid in the vessel is maintained at 37±5° C. Then, after immersing a sample to the center at the bottom of the vessel, the paddle is rotated at a specified position. The test liquid is then collected from the vessel after a specified period of time; this is known as the sample solution. The compounds of interest in the sample solution are then measured using a specified method, and a dissolution rate corresponding to the indicated amount is obtained.

It is essential to ensure stability of the dissolution test.

However, in dissolution testers using conventional techniques, it is difficult to further stabilize the dissolution test. In addition, the factors preventing further stabilization of the dissolution test with the conventional techniques are not well known.

SUMMARY OF THE INVENTION

The present invention has been conceived in light of the above-described problems in the related art. An object thereof is to provide a dissolution tester that can conduct a dissolution test more stably.

<Investigation of Factors Involved>

As a result of extensive investigation into the factors involved in conducting a stable dissolution test, the inventors of the present invention discovered the following problems preventing further stabilization of the dissolution test.

Namely, in order to further stabilize the dissolution test, the inventors found that it is extremely important to make the agitation conditions of the samples and the test liquids uniform, from vessel to vessel, during the dissolution test.

In practice, however, it is extremely difficult to make the agitation conditions of the samples and test liquids uniform from vessel to vessel, and the inventors observed the phenomenon described below.

The dissolution test is normally conducted using a plurality of vessels simultaneously, rather than a single vessel. Naturally, therefore, there are some differences in the agitation conditions of the samples and test liquids in the vessels. As a result, the dissolution rates of the vessels differ, and the inventors found that it may not be possible to conduct the dissolution test stably for a plurality of vessels.

The inventors further investigated eliminating these differences in agitation conditions among the vessels and found that the reason for the differences was different center-axis positions of the paddles relative to the center axes of the vessels.

Based on this knowledge, the inventors realized that proper positioning of the center axes of the paddles relative to the center axes of the vessels, for all vessels, is critical for conducting a stable dissolution test.

For example, the vessels must be set in specific positions in the dissolution tester. This is normally achieved in advance using a tool or measuring instrument to position the center axes of the rotation shafts with the center axes of the vessels and directly securing the vessels. Or, conventionally, guides for ensuring mounting reproducibility may be provided in advance.

However, this centering procedure using a tool or measuring instrument must be carried out for each of the vessels and is therefore time consuming. Furthermore, if the number of vessels is large, the conventional technique is not suitable for centering variations which easily occur for each vessel. Also, if guides are used, the configuration becomes complex.

Therefore, in order to conduct a stable dissolution test in the present invention, it is critical to perform proper centering using a simple configuration.

As a result of extensive investigation of this problem, the inventors conceived the solutions described below.

In order to achieve the object described above, a dissolution tester according to the present invention includes a constant-temperature-water tank, a head, a support arm, a vessel, a water-tank lid, a vessel lid, and a lid-moving shaft.

In the present invention, by moving the lid-moving shaft starting from a position where the vessel lid is raised above the vessel and separated therefrom, when the vessel lid is lowered using the lid-moving shaft to cause the tapered portion of the vessel lid to come into contact with the top opening of the vessel, the vessel is made to move within a predetermined range in the planar direction of the water-tank lid such that the center axis of the lid-moving shaft and the center axis of the vessel are aligned.

The constant-temperature-water tank is provided on a base. The constant-temperature-water tank contains constant-temperature water.

The head is disposed above the constant-temperature-water tank. The head moves up and down relative to the base.

The support arm supports the head so as to allow free movement up and down relative to the base.

The vessel comprises a main body having a bottom and a top opening for inserting a sample and a test liquid, and an outwardly projecting flange disposed around the entire circumference of a peripheral wall defining the top opening of the main body. The desired portion of the main body is immersed into the constant-temperature water inside the constant-temperature-water tank.

The water-tank lid is provided at a top opening of the constant-temperature-water tank. The water-tank lid is provided with a retaining hole having an inner diameter that is slightly larger than the outer diameter of the main body of the vessel and that is slightly smaller than the outer diameter of the flange of the vessel. The water-tank lid holds the vessel by catching the projecting flange of the vessel at the retaining hole such that the desired portion of the vessel is immersed in the constant-temperature water inside the constant-temperature-water tank.

The vessel lid can be attached to and removed from the top opening of the vessel. The vessel lid has a tapered portion having a bottom diameter that is smaller than a top diameter thereof.

The lid-moving shaft is suspended from a lower part of the head and which is aligned with and secured to a center of the vessel lid to move up and down together with the vessel lid.

It is preferable in the present invention that the lid-moving shaft comprises a tube which is secured to the bottom of the head and which is aligned with and secured to the center of the vessel lid such that the center axis of the lid-moving shaft and the center axis of the vessel lid are aligned, and a rotary shaft which is rotatable inside the tube. It is preferable in the present invention to provide a test-liquid agitator for agitating the sample and the test liquid inside the vessel is provided at the bottom of the rotary shaft.

In the present invention, in order to perform the centering procedure more reliably and easily to conduct a stable dissolution test, it is extremely important to protect the flange of each vessel.

When attaching or detaching the vessel to or from the dissolution tester or when cleaning it, it is easily damaged, particularly the flange. Accidentally using a damaged vessel in the dissolution test tends to cause the centering errors described above. Therefore, it may not be possible to conduct the dissolution test stably.

In order to realize the object described above in light of these problems, a vessel used for conducting a dissolution test according to the present invention includes a main body, an outwardly protruding flange, and a protective cover.

The main body has a bottom, as well as a top opening for inserting a sample and a test liquid.

The protruding flange is provided around the entire circumference of the peripheral wall defining the top opening of the main body and projects outward.

The protective cover is formed so as to cover the protruding flange.

The material of the protective cover in the present invention is, for example, resin. The protective cover may be formed as a surface coating or a separate member, for example.

<Effect>

A dissolution tester according to the present invention includes a water-tank lid which holds a vessel in a retaining hole having an inner diameter that is larger than the outer diameter of the main body of the vessel and smaller than the outer diameter of the flange thereof; a vessel lid having a tapered portion; and a lid-moving shaft which is aligned with and secured to the center of the vessel lid so as to move up and down together with the vessel lid. Therefore, it is possible to conduct a stable dissolution test with a simple configuration.

In the present invention, the lid-moving shaft includes a rotary shaft which can rotate inside a tube, which is aligned with and secured to the center of the vessel lid. A test-liquid agitator is also provided at the bottom of the rotary shaft. As a result, it is possible to conduct a stable dissolution test with a more simple configuration.

Because the flange of a vessel according to the present invention is provided with a protective cover, it is possible to conduct a stable dissolution test with a more simple configuration.

DESCRIPTION OF THE PREFERRED EMBODIMENT

A preferred embodiment of the present invention will be described below based on the drawings.

Figure 1:
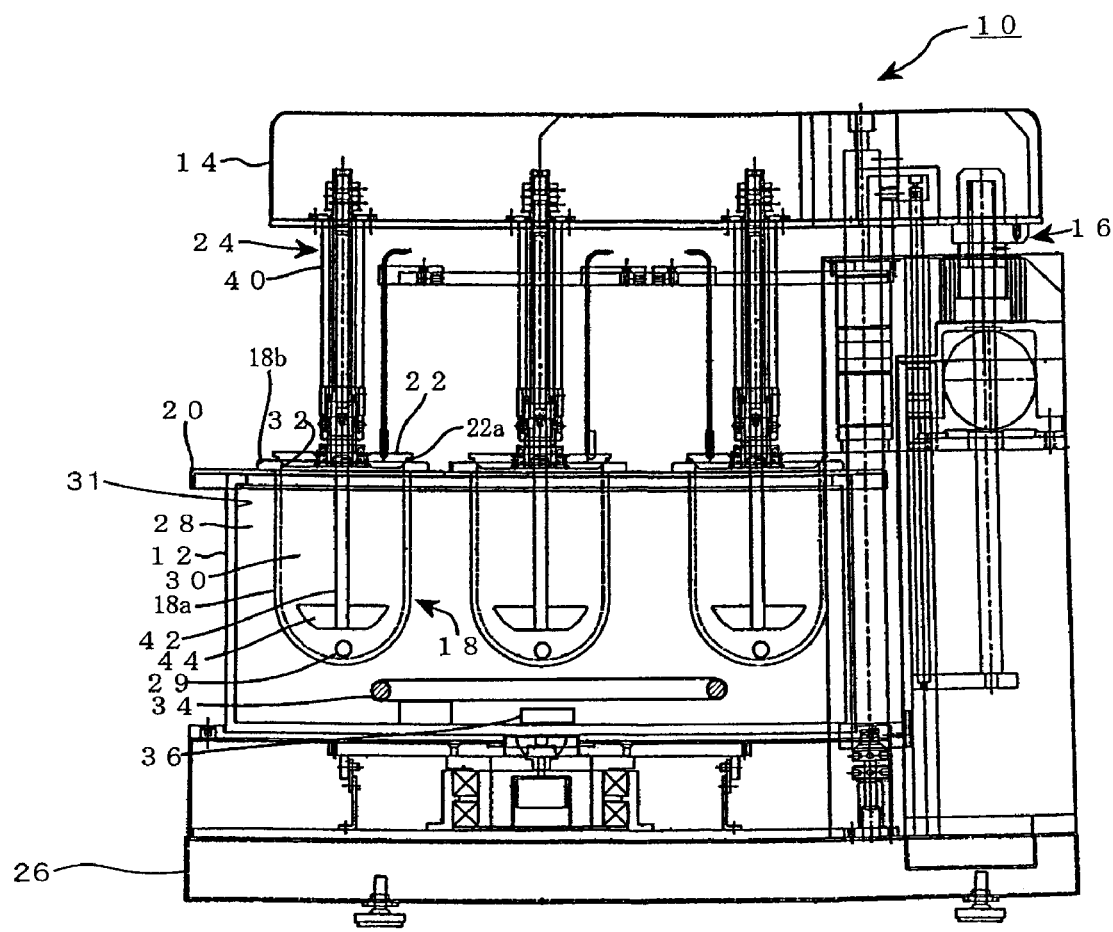
FIG. 1 is a diagram showing an outline configuration of a dissolution tester according to an embodiment of the present invention.

FIG. 1 shows, in outline, the configuration of A dissolution tester 10 according to the embodiment of the present invention.

The dissolution tester 10 shown in FIG. 1 includes a constant-temperature-water tank 12, a head 14, a support arm 16, vessels 18, a water-tank lid 20, vessel lids 22, and lid-moving shafts 24.

The constant-temperature-water tank 12 is provided on a base 26 and is a circular water tank that can hold constant-temperature water 28.

The head 14 is disposed above the constant-temperature-water tank 12 and moves up and down relative to the base 26.

The support arm 16 supports the head 14 in a cantilevered fashion so that it can move up and down relative to the base 26.

The vessels 18 are generally cylindrical, and each vessel 18 has an opening 32 at the top thereof for inserting a sample 29 and a test liquid 30. The vessels 18 each include a main body 18a with a hemispherical bottom, and a flange 18b. The flange 18b is disposed around the entire circumference of the peripheral wall defining the opening 32 at the top of the main body 18a and projects outwards. A desired portion of the main body 18a of each vessel 18 is immersed into the constant-temperature water 28 inside the constant-temperature-water tank 12.

The water-tank lid 20 is disposed at an opening 31 at the top of the constant-temperature-water tank 12. The water-tank lid 20 is provided with retaining holes 33. The retaining holes 33 have inner diameters that are slightly larger than the outer diameters of the main bodies 18a of the vessels 18 and that are slightly smaller than the outer diameters of the flanges 18b of the vessels 18.

The outwardly projecting flanges 18b of the vessels 18 are held at the retaining holes 33, and the water-tank lid 20 supports the vessels 18 so that the desired portions thereof are immersed in the constant-temperature water 28 inside the constant-temperature-water tank 12.

The vessel lids 22 can be attached to and removed from the openings 32 at the top of the vessels 18. The vessel lids 22 have tapered portions 22a whose bottom diameters are smaller than their top diameters.

The lid-moving shafts 24 are suspended from a lower part of the head 14 and are aligned with and secured to the centers of the vessel lids 22. The lid-moving shafts 24 move up and down together with the head 14.

In this embodiment, starting at the position where the vessel lids 22 are raised by the lid-moving shafts 24 to be separated from the vessels 18, the vessel lids 22 are lowered using the lid-moving shafts 24 until the tapered portions 22a of the vessel lids 22 make contact with the openings 32 at the top of the vessels 18. By doing so, the tapered portions 22a of the vessel lids 22 cause the vessels 18 to move within a predetermined region in the planar direction of the water-tank lid (that is, in any horizontal direction) so that the central axes of the lid-moving shafts 24 and the central axes of the vessels 18 are aligned.

<Constant-Temperature-Water Tank>

In this embodiment, a circular heater 34 and a constant-temperature-water agitator 36 are provided for the constant-temperature-water tank 12.

The circular heater 34 is formed in the shape of a circular ring and is disposed concentrically on the bottom inside the circular constant-temperature-water tank 12. The circular heater 34 is used to keep the constant-temperature water 28 at a desired temperature.

The constant-temperature-water agitator 36 includes a stirrer provided at a center at the bottom inside the circular constant-temperature-water tank 12. The constant-temperature-water agitator 36 agitates the constant-temperature water 28 inside the circular constant-temperature-water tank 12 using the stirrer.

<Lid-Moving Shafts>

In this embodiment, the lid-moving shafts 24 each include a tube 40 and a rotary shaft 42.

The lid-moving shafts 24 are secured to the bottom of the head 14, and the outer peripheral walls of the tubes 40 are positioned and secured at the centers of the vessel lids 22 so that the central axes of the lid-moving shafts 24 and the central axes of the vessel lids 22 are aligned.

The rotary shafts 42 can be rotated inside the tubes 40.

Test-liquid agitators 44 are also provided in this embodiment. The test-liquid agitators 44 are formed of paddles. The test-liquid agitators 44 are provided at the lower ends of the rotary shafts 42 and agitate the samples 29 and test liquids 30 inside the vessels 18.

Configuring the dissolution tester 10 in this way allows dissolution of the samples 29 to be performed.

In order to conduct the dissolution test stably, the inventors of the present invention found that it is essential to surely center each vessel 18 using a simple configuration. Using this knowledge, centering is performed in the dissolution tester 10 according to this embodiment, as described below.

Figure 2:
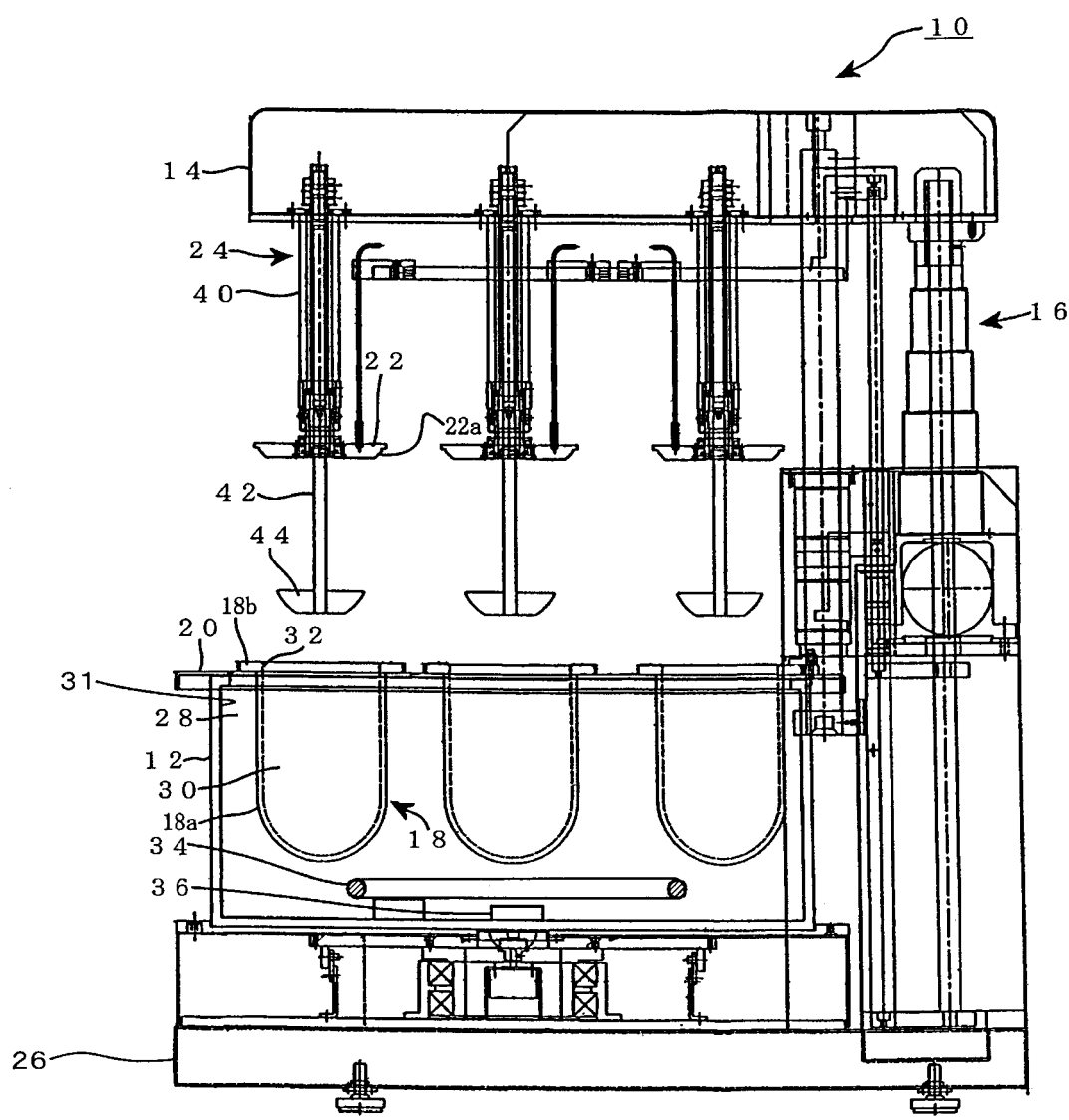
FIG. 2 is a diagram of the dissolution tester shown in FIG. 1, during maintenance.

When performing maintenance of the dissolution tester 10 in this embodiment, the dissolution tester 10 is initially set to a state shown in FIG. 2.

In the dissolution tester 10, as shown in FIG. 2, the vessel lids 22 are raised together with the head 14 and the lid-moving shafts 24 to be separated from the vessels 18. Then, with the dissolution tester 10 in this state, the vessels 18 are replaced. After replacing the vessels 18, it is necessary to position new vessels in the dissolution tester 10.

To carry out this positioning, normally the lid-moving shafts and the vessels are centered in advance using a tool or measuring instrument and the vessels are directly secured. Alternatively, guides for ensuring reproducibility of the mounting operation may be provided.

However, this type of positioning requires a lot of work and is not suitable because centering errors tend to occur from vessel to vessel.

In the conventional method, therefore, because the agitation conditions for the vessels are different, it is difficult to conduct the dissolution test stably.

In contrast, this embodiment has a simple configuration for carrying out this positioning, without requiring a lot of work or a complex configuration. It is described below.

The vessel lids 22 are normally provided only for preventing evaporation of the test liquids 30. In this embodiment, however, in order to simplify the configuration, the vessel lids 22 serve two functions, namely, to prevent evaporation of the test liquids 30 and to position the vessels 18.

In this embodiment, the centers of the vessel lids 22 are prealigned with and secured to the outer peripheral walls of the tubes 40 of the lid-moving shafts 24. By doing so, the test-liquid agitators 44, such as paddles, are combined with and secured to the circular vessel lids 22, which are perpendicular to the rotating shafts 42. In this embodiment, therefore, the vessels lids 22 also move up and down together with the lid-moving shafts 24 when carrying out maintenance.

The circular circumferential portions of the vessel lids 22 are provided with the downwardly tapering tapered portions 22a, which substantially correspond to the openings 32 at the top of the vessels 18.

In addition, in this embodiment, the water-tank lid 20 is provided with the retaining holes 33 for supporting the vessels 18 horizontally while allowing some degree of freedom in the horizontal directions. The diameters of the retaining holes 33 in the water-tank lid 20 are made to be slightly larger than the outer diameters of the vessels 18 so that the vessels 18 can move slightly in the lateral direction when joining the vessel lids 22 and the vessels 18.

Figure 3:
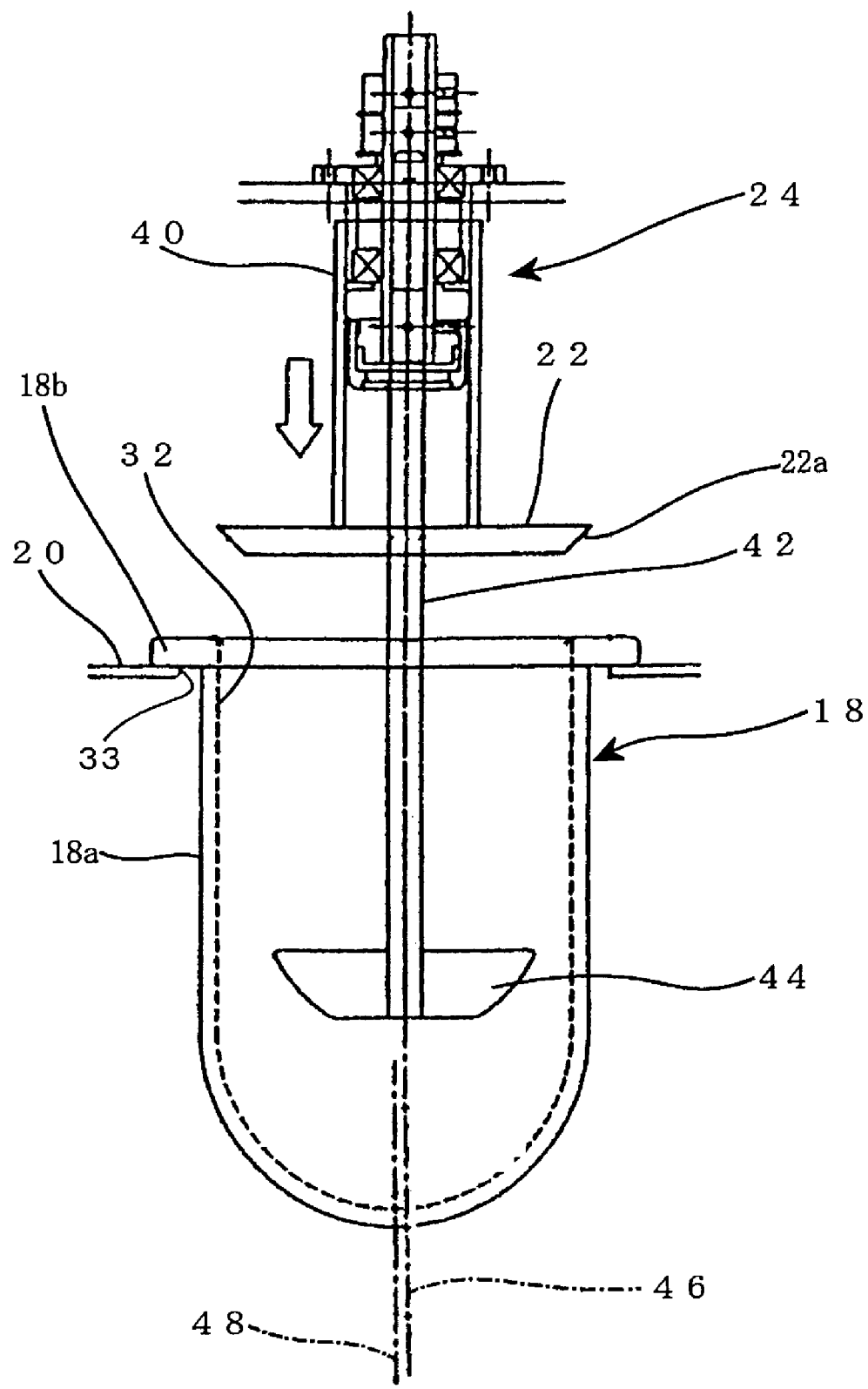
FIG. 3 is a diagram of a positioning mechanism, which is a first characterizing feature of this embodiment.

Therefore, as shown in FIG. 3, once the vessel lids 22 are raised using the lid-moving shafts 24 so that they are separated from the vessels 18, even if the central axes 46 of the lid-moving shafts 24 and the central axes 48 of the vessels 18 are misaligned, lowering the vessel lids 22 using the lid-moving shafts 24 causes the tapered portions 22a of the vessel lids 22 to come into contact with the openings 32 at the top of the vessels 18. This results in automatic alignment, as described below.

Figure 4:
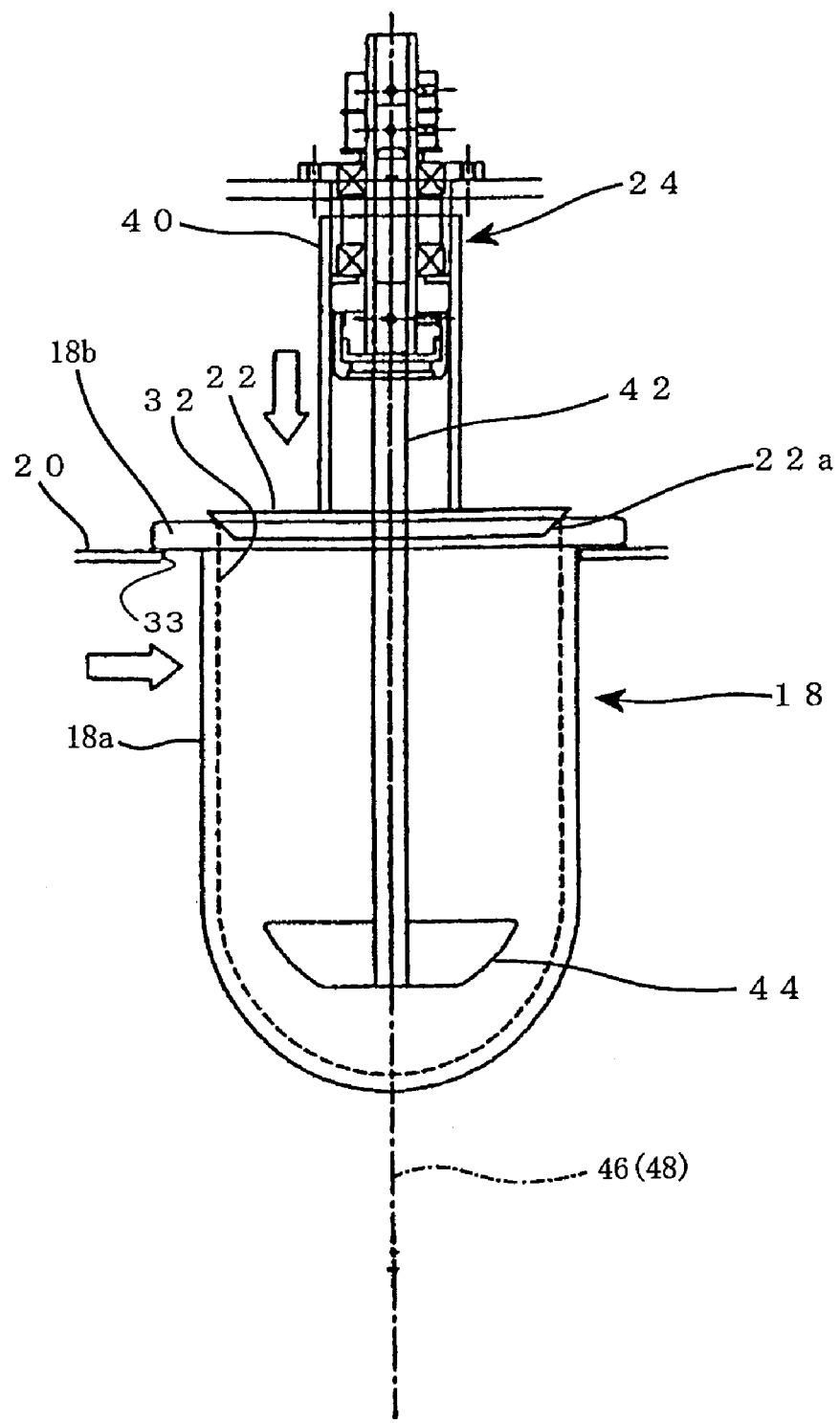
FIG. 4 is a diagram for explaining the operation of the positioning mechanism, which is the first characterizing feature of this embodiment.

As shown in FIG. 4, merely by lowering the vessel lids 22, the tapered portions 22a of the vessel lids 22 move the vessels 18 relative to the water-tank lid 20, namely, to the right in the figure within the retaining holes 33, and this causes the central axes of the lid-moving shafts 24 and the central axes of the vessels 18 to become automatically aligned.

As a result, even if the vessels 18 are replaced with vessels whose cylindrical portions (the main bodies 18a) have different diameters, it is possible to always automatically align the centers of the test-liquid agitators 44, such as paddles, with the centers of the vessels 18 simply by lowering the test-liquid agitators 44. Therefore, special centering adjustment is not required in this embodiment.

Accordingly, in this embodiment, it is possible to reliably center each vessel 18 using a simple configuration. The centering uniformity of the vessels 18 is thus improved, and because the agitation conditions in the vessels 18 can be made more uniform in this embodiment, it is possible to conduct the dissolution test more stably.

<Protective Cover>

Figure 5:
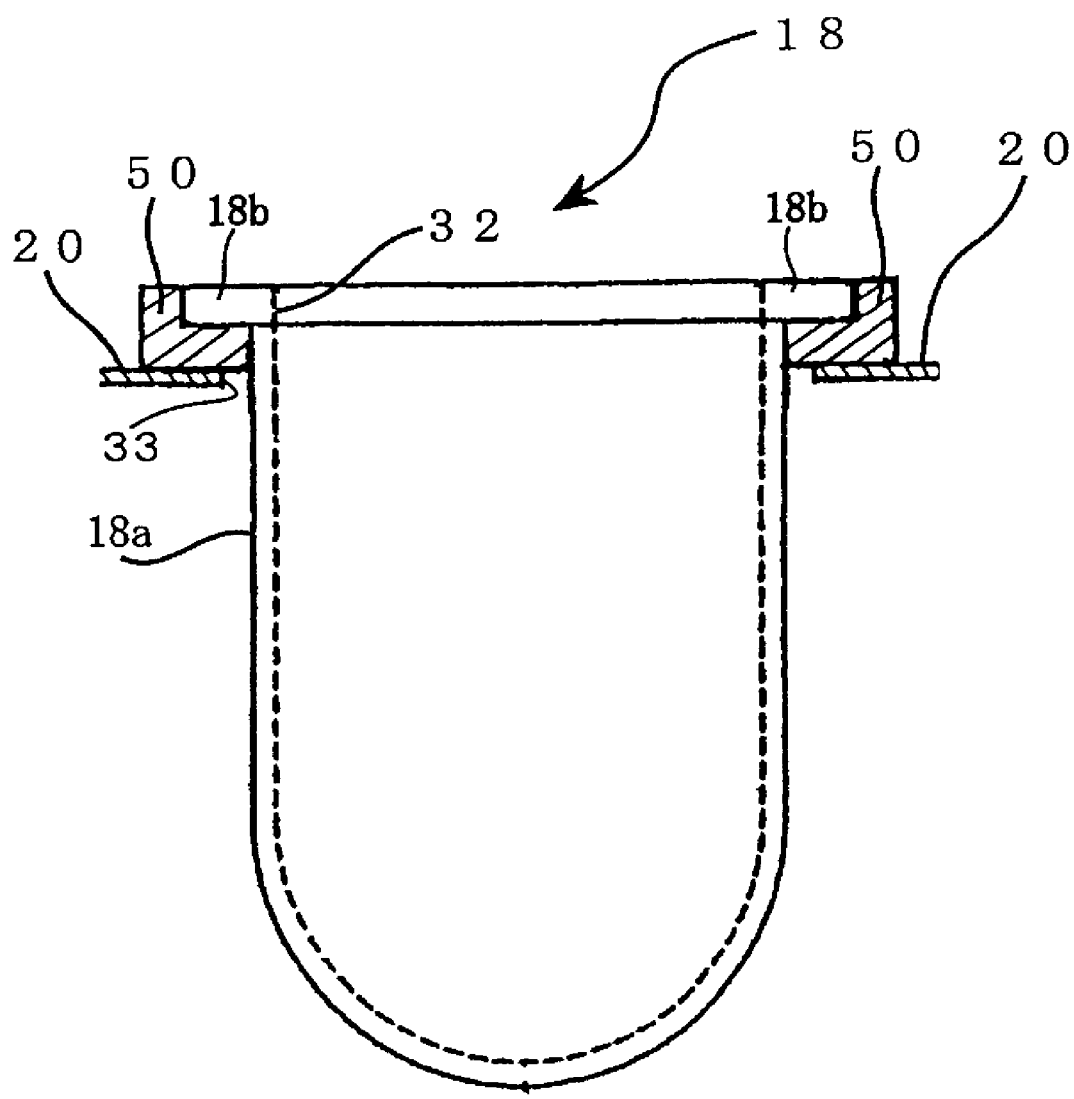
FIG. 5 is a diagram of a vessel, which is a second characterizing feature of this embodiment.

In this embodiment, it is particularly preferable to use a vessel 18 shown in FIG. 5 in order to conduct the dissolution test more stably.

The vessel 18 shown in FIG. 5 includes a main body 18a, an outwardly protruding flange 18b, and a protective cover 50.

The main body 18a has a bottom, as well as a top opening 32 for inserting a sample 29 and a test liquid 30.

The protruding flange 18b is provided around the entire circumference of the peripheral wall defining the opening 32 at the top of the main body 18a, and protrudes outwardly.

The protective cover 50 is provided so as to cover the protruding flange 18b.

Examples of the protective cover 50 in this invention include a member or coating made of resin, for instance.

During maintenance, and naturally during the dissolution test as well, the vessel 18 in this embodiment is handled with the protective cover 50 attached.

Therefore, the protective cover 50 can surely prevent the flange 18b of the vessel 18 from becoming chipped during maintenance, for example, when cleaning the vessel 18. As a result, it is always possible to use the vessel 18 at an undamaged condition, and in addition, handling of the vessel 18 is facilitated.

When automatically centering the vessels 18 using the vessel lids 22, as described above, the protective covers 50 can largely reduce the risk of breakage of the vessels 18, particularly the flanges 18b, caused by pressure from the vessel lids 22.

In this embodiment, the protective covers 50 are thus provided for the vessels 18 for handling. Doing so allows the uniformity of the vessels 18 used in the dissolution test to be reliably ensured, and therefore, the dissolution test can be carried out more stably.

Modifications

<Measurement Method>

Although the above configurations have been illustrated by using a paddle method, the present invention is not limited to this. It is possible to use a basket method in which the sample 29 is placed in a basket.

More specifically, although the above configurations have been illustrated using an example in which paddles are provided on the rotary shafts 42, the present invention is not limited to this. The configuration described below may also be used.

Instead of paddles, it is also preferable to provide rotating baskets on the rotary shafts 42. In this case, it is preferable to lower the baskets to a specified position in the vessels 18 and to rotate the baskets, containing the samples 29, in the test liquids 30 inside the vessels 18.

<Dosage Form>

The above configurations have been illustrated by using tablets as the dosage form of the samples 29; however, the present invention is not limited to this. It is possible to use other suitable dosage forms, such as capsules, granules, or powder.

What is claimed is:

1. A dissolution tester comprising:
a constant-temperature-water tank provided on a base and containing constant-temperature water;
a head disposed above the constant-temperature-water tank, which moves up and down relative to the base;
a support arm for supporting the head so as to allow free movement up and down relative to the base;
a vessel comprising a main body having a bottom and a top opening for inserting a sample and a test liquid, and an outwardly projecting flange disposed around the entire circumference of a peripheral wall defining the top opening of the main body, a desired portion of the main body being immersed into the constant-temperature water inside the constant-temperature-water tank;
a water-tank lid which is provided at a top opening of the constant-temperature-water tank, which is provided with a retaining hole having an inner diameter that is slightly larger than the outer diameter of the main body of the vessel and that is slightly smaller than the outer diameter of the flange of the vessel, and which holds the vessel by catching the projecting flange of the vessel at the retaining hole such that the desired portion of the vessel is immersed in the constant-temperature water inside the constant-temperature-water tank;
a vessel lid which can be attached to and removed from the top opening of the vessel, wherein the lid prevents evaporation of the test liquids in the vessel, when the lid is attached to the top opening of the vessel, which moves up and down relative to the vessel, said vessel lid including a tapered portion having a bottom diameter that is smaller than a top diameter thereof which serves to position the vessel relative to the lid as the lid is being attached to the vessel; and
a lid-moving shaft which is suspended from a lower part of the head and which is aligned with and secured to a center of the vessel lid to move up and down together with the vessel lid,
wherein, by moving the lid-moving shaft starting from a position where the vessel lid is raised above the vessel and separated therefrom, when the vessel lid is lowered using the lid-moving shaft to cause the tapered portion of the vessel lid to come into contact with the top opening of the vessel, the vessel is made to move within a predetermined range in the planar direction of the water-tank lid such that the center axis of the lid-moving shaft and the center axis of the vessel are aligned and the vessel lid closes the vessel.

2. The dissolution tester of claim 1, wherein the vessel comprises
the main body having the bottom and the top opening for inserting the sample and the test liquid;
the outwardly protruding flange provided around the entire circumference of the peripheral wall defining the top opening of the main body; and
a protective cover provided so as to cover the protruding flange.

3. The dissolution tester of claim 1, wherein
the lid-moving shaft comprises
a tube which is secured to the bottom of the head and which is aligned with and secured to the center of the vessel lid such that the center axis of the lid-moving shaft and the center axis of the vessel lid are aligned; and
a rotary shaft which is rotatable inside the tube, and
a test-liquid agitator for agitating the sample and the test liquid inside the vessel is provided at the bottom of the rotary shaft.

4. The dissolution tester of claim 3, wherein the vessel comprises
the main body having the bottom and the top opening for inserting the sample and the test liquid;
the outwardly protruding flange provided around the entire circumference of the peripheral wall defining the top opening of the main body; and
a protective cover provided so as to cover the protruding flange.

* * * * *